United States Patent
De Wijn et al.

(10) Patent No.: US 8,962,268 B2
(45) Date of Patent: Feb. 24, 2015

(54) METHOD FOR DETERMINING SURVIVAL PROGNOSIS OF PATIENTS SUFFERING FROM NON-SMALL CELL LUNG CANCER (NSCLC)

(75) Inventors: Richard De Wijn, Nijmegan (NL); Robby Ruijtenbeek, Utrecht (NL); Maria Helena Hilhorst, Wageningen (NL)

(73) Assignee: Pamgene B.V., 's-Hertogenbosch (NL)

(*) Notice: Subject to any disclaimer, the term of this patent is extended or adjusted under 35 U.S.C. 154(b) by 400 days.

(21) Appl. No.: 13/138,849

(22) PCT Filed: Apr. 12, 2010

(86) PCT No.: PCT/EP2010/054763
§ 371 (c)(1),
(2), (4) Date: Oct. 7, 2011

(87) PCT Pub. No.: WO2010/115997
PCT Pub. Date: Oct. 14, 2010

(65) Prior Publication Data
US 2013/0017963 A1     Jan. 17, 2013

(30) Foreign Application Priority Data
Apr. 10, 2009 (EP) .................... 09157816

(51) Int. Cl.
*G01N 33/00* (2006.01)
*C12Q 1/48* (2006.01)
*G01N 33/574* (2006.01)
*G01N 33/48* (2006.01)
(Continued)

(52) U.S. Cl.
CPC .......... *G01N 33/57423* (2013.01); *C12Q 1/485* (2013.01)

USPC .................. 435/7.92; 435/15; 436/64; 506/9; 506/10

(58) Field of Classification Search
None
See application file for complete search history.

(56) References Cited

U.S. PATENT DOCUMENTS

2005/0187147 A1* 8/2005 Newman et al. ................... 514/8
2006/0252056 A1* 11/2006 Tsuruo et al. ..................... 435/6
(Continued)

FOREIGN PATENT DOCUMENTS

WO    2007005027 A1    1/2007
WO    2008049930 A2    5/2008

OTHER PUBLICATIONS

Lemeer, S; Jopling, C; Naji, F; Ruijtenbeek, R; Slijper, M; Heck, A.J.R.; den Hertog, J "Protein-Tyrosine Kinase Activity Profiling in Knock Down Zebrafish Embryos." PLoS ONE, Jul. 4, 2007, 2(7): e581, 6 pages and supplemental information (table S1, 2 pages).*

(Continued)

*Primary Examiner* — Jon P Weber
*Assistant Examiner* — Aaron J Kosar
(74) *Attorney, Agent, or Firm* — Amster, Rothstein & Ebenstein LLP

(57) ABSTRACT

The present invention relates to a method for determining the survival prognosis of patients suffering from non-small cell lung cancer. More specifically, the present invention provides methods which measure kinase activity by studying phosphorylation levels in response to a kinase inhibitor and profiles in samples obtained from patients diagnosed with non-small cell lung cancer. The present invention also provides methods for predicting the response of a patient diagnosed with non-small cell lung cancer to a medicament.

8 Claims, 1 Drawing Sheet

(51) Int. Cl.
  *C40B 30/06* (2006.01)
  *C40B 30/08* (2006.01)

(56) References Cited

U.S. PATENT DOCUMENTS

2007/0148711 A1  6/2007  Rikova et al.
2010/0234238 A1  9/2010  Versele et al.

OTHER PUBLICATIONS

AstraZeneca "IRESSA®: gefitinib tablets" IRESSA label, NDA 21-399/S-008, Apr. 7, 2004 (FDA archived Jun. 17, 2005), pp. 3-14.*
de Wijn, R et al "PamChip® microarrays and PamStation® Instruments; A Novel Platform to Support Kinase and Kinase Inhibitor Research", Application Note—Protein Kinases; Technology Outline (No. 201002), Sep. 2010, 1 page.*
Schutkowski, M., Reimer, U., Panse, S., Dong, L., Lizcano, J. M., Alessi, D. R. and Schneider-Mergener, J. "High-Content Peptide Microarrays for Deciphering Kinase Specificity and Biology" Angew. Chem. Int. Ed., 2004 (published online May 5, 2004), 43, pp. 2671-2674 (and supporting information pp. s1-s13).*
Han, Xiaoming, et al, "A Quantitative Peptide Array for Evaluation of Protein Kinase Activity" Anal. Biochem., Jan. 1, 2008, 372(1), pp. 106-115.*
Tang J M et al., entitled "Phosphorylated Akt overexpression and loss of PTEN expression in non-small cell lung cancer confers poor prognosis," Lung Cancer, 2006, 51, 181-191.
Vanmeter A J et al., entitled "Laser Capture Microdissection and Protein Microarray Analysis of Human Non-small Cell Lung Cancer," Molecular & Cellular Proteomics, 2008, 7.10, 1902-1924.
PCT Notification of Transmittal of the International Search Report and the Written Opinion of the International Searching Authority, or the Declaration issued by the European Patent Office in connection with PCT International Patent Application No. PCT/EP2010/054763, Oct. 1, 2010, 14 pages.
PCT Notification of Transmittal of the International Preliminary Report dated Mar. 22, 2011 from the European Patent Office in connection with PCT International Patent Application No. PCT/EP2010/054763, 11 pages.

* cited by examiner

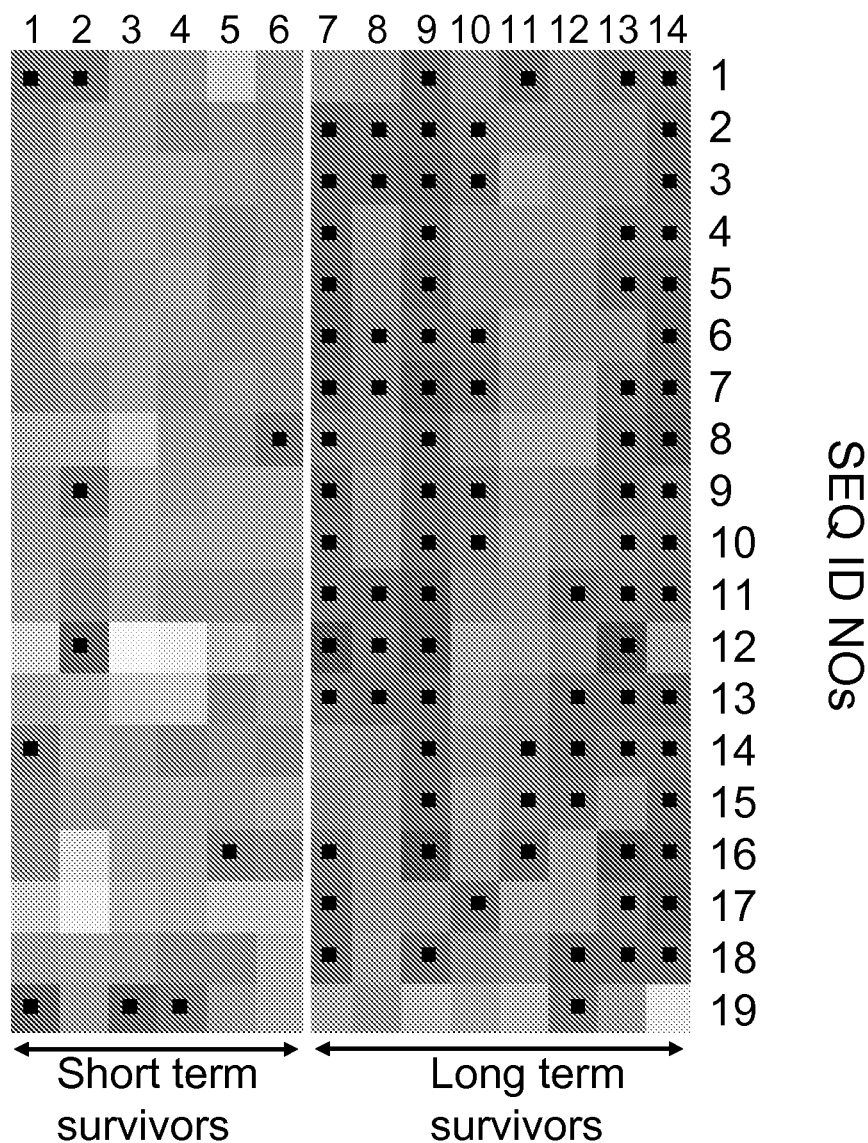

US 8,962,268 B2

METHOD FOR DETERMINING SURVIVAL PROGNOSIS OF PATIENTS SUFFERING FROM NON-SMALL CELL LUNG CANCER (NSCLC)

CROSS-REFERENCE TO THE RELATED APPLICATIONS

This application is a U.S. national stage entry under 35 U.S.C. §371 of PCT International Patent Application No. PCT/EP2010/054763, filed Apr. 12, 2010, and claims priority to European Patent Application No. 09157816.1 filed Apr. 10, 2009, the contents of which are incorporated herein by reference in their entirety.

FIELD OF THE INVENTION

The present invention relates to a method for determining the survival prognosis of patients suffering from non-small cell lung cancer. More specifically, the present invention provides methods which measure kinase activity by studying phosphorylation levels and profiles in samples obtained from patients diagnosed with non-small cell lung cancer.

BACKGROUND OF THE INVENTION

At present lung cancer is considered to be one of the most important causes of death, especially in adults at the ages from 50 to 69 years old. Long term exposure to smoking is the cause of lung cancer for 90% of the cases. Among male smokers, the lifetime risk of developing lung cancer is about 17%; among female smokers the risk is about 11%. For non-smokers, the risk of developing lung cancer is about 1%. The main causes for lung cancer in non-smokers are genetic factors, radon gas, asbestos, air pollution and passive smoking. There are two main types of lung cancer: non-small cell lung cancer (NSCLC) (in about 80% of the cases) and small cell lung cancer (in about 17% of the cases). NSCLC can further be classified according to the growth type and spread of the cancer cells. NSCLC can therefore be classified into squamous cell carcinoma, large cell carcinoma and adenocarcinoma. Adenocarcinoma is more frequent in women, Asians and non-smokers. Other less common types of NSCLC are pleomorphic, carcinoid tumor, salivary gland carcinoma, and unclassified carcinoma.

It is generally known that most types of lung cancer have a poor prognosis. The 5 year survival for small cell lung cancer is less than 5%. Numbers are better for NSCLC. When the tumor is detected when it is still small and has not spread to the lymph nodes (Stage IA), the 5 year survival is 60%. This number drops rapidly with increasing size of the tumor and lymph node involvement. An early detection prior to the metastasis of the tumor is therefore very important, especially since at an early stage the tumor may be removed entirely by resection. However, about 50% of non-small cell lung cancer cases are only detected after metastasis. In these cases the 5-year survival of NSCLC is only 10 to 15%. Even when NSCLC is detected at an early stage, the 5-year survival rate of the patients is low compared to other types of cancer. Even more, it is known that long-term (>5 years) NSCLC patients do not experience the same length of life and quality of life as their age-matched peers or other cancer survivors.

When NSCLC is detected at an early stage (IA to IIIA), the tumor is resected. The resection is followed by chemotherapy for larger tumors and in case the tumor has spread to the lymph nodes (stages II and IIIA). Patients in stage I receive no further treatment. Although these patients have a good prognosis based on tumor staging, a large percentage of patients develop metastases within several months or years. The consequence is a short survival time after resection. For this group of patients, follow up treatment would be beneficial. On the other hand, a substantial number of patients is cured and have a long survival period. For this group of patients, follow up treatment brings no benefit but only the side effects associated with the treatment. The options for further treatment are chemotherapy or targeted therapy with a kinase inhibitor like gefitinib. Side effects of chemotherapy are severe and also a rather mild therapy like treatment with gefitinib can have very unpleasant side effects. Therefore, it is no option to subject all persons diagnosed with lung cancer to adjuvant therapy after surgery.

There remains a pressing need for methods that provide good clinical predictions of the progression of NSCLC. These methods would enable the identification of NSCLC patients at an early stage, and more specifically provide an early determination of the prognosis of NSCLC. Additionally NSCLC patients with a poor survival prognosis might benefit from specific adjuvant therapies whereas other therapies might be more beneficial for NSCLC patients with a good survival prognosis.

The present invention aims at providing methods and devices for determining the survival prognosis of patients suffering from NSCLC. The present invention also aims to provide methods and devices for predicting the response of a patient diagnosed with NSCLC to a medicament.

SUMMARY OF THE INVENTION

The present invention provides methods and devices that enable the determination of the survival prognosis of patients suffering from non-small cell lung cancer based on the measurement of the kinase activity of a non-small cell lung tumor sample.

The present invention therefore provides a method for determining a survival prognosis of a patient suffering from non-small cell lung cancer. In a first embodiment of the present invention, the method comprises the steps of:

(a) measuring kinase activity of a sample, obtained from the non-small cell lung tumor from said patient, in the presence and in the absence of a protein kinase inhibitor, preferably gefitinib, thereby providing a phosphorylation profile of said sample in the presence of a protein kinase inhibitor and a phosphorylation profile of said sample in the absence of a protein kinase inhibitor; and, (b) determining from said phosphorylation profiles in the presence and in the absence of a protein kinase inhibitor a differential phosphorylation level, said differential phosphorylation level indicating the survival prognosis of said patient.

Another embodiment of the present invention relates to a method for predicting the response of a patient diagnosed with non-small cell lung cancer to a medicament, wherein the kinase activity of a sample obtained from a non-small cell lung tumor from said patient, is measured in the presence and in the absence of said medicament and wherein said kinase activity in the presence of said medicament is compared to the kinase activity in the absence of said medicament thereby determining the response of said patient to said medicament, and wherein said kinase activity measurement provides phosphorylation profiles of said sample in the presence and in the absence of said medicament.

More preferably the phosphorylation profiles obtained in the methods of the present invention comprise the phosphorylation levels of, preferably one or more, phosphorylation sites present in any of the peptide markers as listed in table 1.

The present invention also relates in another embodiment to an array for carrying out the method of the present invention, said array comprising immobilized proteins, peptides or peptide mimetics comprising, preferably one or more, phosphorylation sites present in any of the peptide markers as listed in table 1. Said proteins, peptides or peptide mimetics are preferably at least 25% of proteins, peptides or peptide mimetics on said array.

The present invention further relates in yet another embodiment to a method for determining the survival prognosis of a patient suffering from non-small cell lung cancer, comprising the steps of:

(a) measuring kinase activity of a sample, obtained from a non-small cell lung tumor from said patient, in the presence and in the absence of a protein kinase inhibitor, thereby providing the phosphorylation level of, preferably one or more, phosphorylation sites present in one of the peptide markers as listed in table 1; and, (b) determining from said phosphorylation level in the presence and in the absence of a protein kinase inhibitor the survival prognosis of said patient.

These and further aspects and embodiments are described in the following sections and in the claims.

BRIEF DESCRIPTION OF FIGURES

FIG. 1 provides a heatmap as depicted in the examples representing the ratio of inhibited versus not inhibited phosphorylation signals for each of the peptide markers listed in Table 1.

DETAILED DESCRIPTION OF THE INVENTION

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods and devices that enable the determination of the survival prognosis of patients suffering from non-small cell lung cancer based on the measurement of the kinase activity of a non-small cell lung tumor sample. Preferably, in one embodiment of the present invention, methods are provided wherein the kinase activity is protein kinase activity. For purposes of the present invention, and as used herein the term "enzyme activity", "kinase activity" or "protein kinase activity" refer to the formation of reaction product(s) by a certain amount of enzyme, kinase or protein kinase acting on a substrate during the course of the assay.

Protein kinase activity is referred to as the activity of one or more protein kinases. A protein kinase is a generic name for all enzymes that transfer a phosphate to a protein. About three to four percent of the human genome contains transcription information for the formation of protein kinases. Currently, there are about 518 known different protein kinases. However, because three to four percent of the human genome is a code for the formation of protein kinases, there may be many more separate kinases in the human body.

A protein kinase is a kinase enzyme that modifies other proteins by covalently coupling phosphate groups to them. This process or activity is also referred to as phosphorylation. Phosphorylation can therefore be regarded as the process of the addition of a phosphate group to a substrate. Phosphorylation usually results in a functional change of the substrate by changing enzyme activity, cellular location, or association with other proteins. Up to 30% of all proteins may be modified by kinase activity, and kinases are known to regulate the majority of cellular pathways, especially those involved in signal transduction, the transmission of signals within the cell. The chemical activity of a kinase involves removing a phosphate group from ATP or GTP and covalently attaching it to amino acids such as serine, threonine, tyrosine, histidine, aspartic acid and/or glutamic acid that have a free hydroxyl group. Most known kinases act on both serine and threonine, others act on tyrosine, and a number act on all serine, threonine and tyrosine. The protein kinase activity monitored with the method of the present invention is preferably directed to protein kinases acting towards serine, threonine and/or tyrosine, preferably acting on both serine and threonine, on tyrosine or on serine, threonine and tyrosine. More preferably the method of the present invention is preferably directed to protein kinases acting towards tyrosines.

Protein kinases are distinguished by their ability to phosphorylate substrates on discrete sequences. These sequences have been determined by sequencing the amino acids around the phosphorylation sites and are usually distinct for each protein kinase. The recognition sequence on each substrate is specific for each kinase catalyst.

Because protein kinases have profound effects on a cell, their activity is highly regulated. Kinases are turned on or off by for instance phosphorylation, by binding of activator proteins or inhibitor proteins, or small molecules, or by controlling their location in the cell relative to their substrates. Deregulated kinase activity is a frequent cause of disease, particularly cancer, where kinases regulate many aspects that control cell growth, movement and death. Therefore monitoring the protein kinase activity in tissues can be of great importance and a large amount of information can be obtained when comparing the kinase activity of different tissue samples.

As described in the present invention, the inventors have surprisingly found that the survival prognosis of non-small cell lung cancer can be predicted and/or determined on the basis of the measurement of the kinase activity of a non-small cell lung tumor sample.

The measurement of the kinase activity is performed by contacting a non-small cell lung tumor sample with one or more substrates, preferably protein kinase substrates, thereby generating a phosphorylation profile.

Said protein kinase substrates as used herein, are preferably peptides, proteins or peptide mimetics. The protein kinase substrates each comprise, preferably one or more, phosphorylation sites that can be phosphorylated by the protein kinases present in the sample. Therefore, exposure of a protein kinase substrate to a sample comprising a protein kinase results in the phosphorylation of one or more of the phosphorylation sites of the protein kinase substrate. This phosphorylation activity can be measured using techniques known in the art. Therefore, during the measurement method the kinase enzymes present in the sample will phosphorylate, preferably one or more, of the phosphorylation sites on one or more protein kinase substrates. The inventors have observed essential differences between the kinase activity of NSCLC patients having a different survival prognosis. Consequently, the inventors have observed that the kinases present in a NSCLC sample will phosphorylate protein kinase substrates depending on the survival prognosis of said patient. Phosphorylation signals differ between the samples, resulting in phosphorylation patterns that differ depending on the survival prognosis. The effect has been observed to be even more significant when measurements in the absence of a protein kinase inhibitor are compared to measurements in the presence of a protein kinase inhibitor.

The present invention therefore provides a method for determining the survival prognosis of a patient suffering from non-small cell lung cancer. In a first embodiment of the present invention, the method comprises the steps of:

(a) measuring the kinase activity of a sample, obtained from the non-small cell lung tumor from said patient, in the presence and in the absence of a protein kinase inhibitor, thereby providing a phosphorylation profile of said sample in the presence of a protein kinase inhibitor and a phosphorylation profile of said sample in the absence of a protein kinase inhibitor; and, (b) determining from said phosphorylation profiles in the presence and in the absence of a protein kinase inhibitor the differential phosphorylation level, said differential phosphorylation level indicating the survival prognosis of said patient.

As referred to in the present application non-small cell lung cancer (NSCLC) regards a specific type of lung cancer. About 8 out of 10 cases of all lung cancers are of the non-small cell type. There are 3 sub-types of NSCLC: squamous cell carcinoma, adenocarcinoma and large-cell or undifferentiated carcinoma. Other less common types of NSCLC are pleomorphic, carcinoid tumor, salivary gland carcinoma, and unclassified carcinoma.

As used in the present invention, the term "sample" refers to a sample obtained from an organism (patient) such as human or from components (e.g. tissue or cells) of such an organism. Said sample is preferably obtained from a patient diagnosed with NSCLC and needs to be derived from the tumor tissue of said patient. More preferably said sample is a NSCLC tumor tissue biopsy, vacuum assisted biopsy, fine needle biopsy or material from a resected tumor. Said sample is thereby referred to as a 'clinical sample' which is a sample derived from a NSCLC patient.

Said tumor tissue sample is preferably a fresh or a fresh frozen sample.

More preferably, said sample refers to a lysate of a NSCLC tumor tissue obtained through tumor tissue biopsy, fine needle biopsy or material from a resected tumor. Alternatively said sample may be obtained from specific NSCLC tumor cell lines and in particular cell lysates thereof.

Alternatively said sample may be derived from a tumor sample that has been cultured in vitro for a limited period of time.

In a preferred embodiment of the present invention said sample is a sample that has undergone a preparation step prior to the steps according to the method of the present invention. Preferably said preparation step is a step where the protein kinases present in said sample are released from the tissue by lysis. Additionally the kinases in the sample may be stabilized, maintained, enriched or isolated, and the measurement of the kinase activity as performed in step (a) occurs on the enriched or isolated protein kinase sample. By first enriching protein kinases in the sample or isolating protein kinases from the sample the subsequent measurement of the kinase activity will occur in a more efficient and reliable manner. Also the clarity and intensity of the obtained phosphorylation signal will be increased as certain contaminants are being removed during the enriching or isolating step.

As used in the present invention, the term "phosphorylation profile" refers to a data set representative for the phosphorylation levels of, preferably one or more, phosphorylation sites present on the protein kinase substrates. When measuring the kinase activity of a sample by contacting said sample with protein kinase substrates a specific phosphorylation profile is obtained. The phosphorylation profile is generated by the phosphorylation of the protein kinase substrates with the protein kinases present in the sample and it comprises the level of phosphorylation of the phosphorylation sites present on the protein kinase substrates used. A phosphorylation profile can thus be generated when using at least one protein kinase substrate in different test conditions such as for example by comparing the phosphorylation of a sample on one peptide or protein (protein kinase substrate) in the presence and absence of a protein kinase inhibitor. More frequently phosphorylation profiles of a sample will be measured using several protein kinase substrates in the same or sequentially carried out experiments. Preferably, the present invention determines tyrosine kinase activity levels or profiles.

It should be noted that a person skilled in the art will appreciate that the methods of the present invention can use phosphorylation profiles as a basis for determining the survival prognosis or predicting the response to a medicament of a patient suffering from non-small cell lung cancer. However, the phosphorylation levels of individual protein kinase substrates can also be used as a basis for determining the survival prognosis or predicting the response to a medicament of a patient suffering from non-small cell lung cancer.

It should be noted that for the measurement of the protein kinase activity, ATP or any other phosphate source needs to be added to the sample when it is contacted with the protein kinase substrates. The presence of ATP will lead to a phosphorylation of the protein kinase substrates. Alternatively, the phosphorylation of the protein kinase substrates can be performed in the absence of exogenous ATP. When no ATP is added during the incubation of the sample with the protein kinase substrates, the endogenous ATP, the ATP naturally present in the sample, will act as the primary source of ATP.

The phosphorylation level of each of the protein kinase substrates can be monitored using any method known in the art. The response of the protein kinase substrates is determined using a detectable signal, said signal resulting from the interaction of the sample with the protein kinase substrates or by for instance measuring mass differences using mass spectrometry. In determining the interaction of the sample with the protein kinase substrates the signal is the result of the interaction of the phosphorylated substrates with a detectably labelled molecule capable of binding to the phosphorylated substrates. For the latter, the molecule that specifically binds to the substrates of interest (e.g. antibody or polynucleotide probe) can be detectably labelled by virtue of containing an atom (e.g. radionuclide), molecule (e.g. fluorescein), or enzyme or particle or complex that, due to a physical or chemical property, indicates the presence of the molecule. A molecule may also be detectably labelled when it is covalently bound to or otherwise associated with a "reporter" molecule (e.g. a biomolecule such as an enzyme) that acts on a substrate to produce a detectable atom, molecule or other complex.

Detectable labels suitable for use in the present invention include any composition detectable by spectroscopic, photochemical, biochemical, immunochemical, electrical, optical or chemical means. Labels useful in the present invention include biotin for staining with labelled avidin or streptavidin conjugate, magnetic beads (e.g. Dynabeads'), fluorescent dyes (e.g. fluorescein, fluorescein-isothiocyanate (FITC), Texas red, rhodamine, green fluorescent protein, enhanced green fluorescent protein and related proteins with other fluorescence emission wavelengths, lissamine, phycoerythrin, Cy2, Cy3, Cy3.5, Cy5, Cy5.5, Cy7, FluorX [Amersham], SYBR Green 1 & 11 [Molecular Probes], and the like), radiolabels (e.g. 3H, 125I, 35S, 14C, or 32P), enzymes (e.g. hydrolases, particularly phosphatases such as alkaline phosphatase, esterases and glycosidases, or oxidoreductases, particularly peroxidases such as horse radish peroxidase, and the like), substrates, cofactors, chemilluminescent groups, chromogenic agents, and colorimetric labels such as colloidal gold or coloured glass or plastic (e. g. polystyrene, polypropylene, latex, etc.), protein particles or beads.

Means of detecting such labels are well known to those of skill in the art. Thus, for example, chemiluminescent and radioactive labels may be detected using photographic film or scintillation counters, and fluorescent markers may be detected using a photodetector to detect emitted light (e.g. as in fluorescence-activated cell sorting). Enzymatic labels are typically detected by providing the enzyme with a substrate and detecting a coloured reaction product produced by the action of the enzyme on the substrate. Colorimetric labels are detected by simply visualizing the coloured label. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the colour associated with the label. Fluorescence resonance energy transfer has been adapted to detect binding of unlabeled ligands, which may be useful on arrays.

In a particular embodiment of the present invention the response of the protein kinase substrates to the sample is determined using detectably labelled antibodies; more in particular fluorescently labelled antibodies. In those embodiments of the invention where the substrates consist of protein kinase substrates, the response of the protein kinase substrates is determined using fluorescently labelled anti-phosphotyrosine antibodies, fluorescently labelled anti-phosphoserine or fluorescently labelled anti-phosphothreonine antibodies. The use of fluorescently labelled anti-phosphotyrosine antibodies or fluorescently labelled anti-phosphoserine or fluorescently labelled anti-phosphothreonine antibodies in the method of the present invention, allows real-time or semi real-time determination of the protein kinase activity and accordingly provides the possibility to express the protein kinase activity as the initial velocity of protein kinase derived from the activity over a certain period of incubation of the sample on the protein kinase substrates.

The inventors have found that measuring the kinase activity of the sample in the presence and in the absence of a protein kinase inhibitor, enables an even better differentiation between the different survival prognoses of NSCLC patients. This surprising effect is due to the differences in protein kinase activity between different individual patients and their respective tumors. The difference can be reduced by comparing the protein kinase activity profiles in the presence and absence of a protein kinase inhibitor between different patients. This enables a more accurate classification of the survival prognosis and moreover a smaller number of protein kinase substrates will be needed to determine the survival prognosis of NSCLC patients, and preferably patients with an early stage of NSCLC.

The term "differential phosphorylation level" as used herein therefore refers to a data set comprising comparison data from the phosphorylation profiles in the presence and in the absence of a protein kinase inhibitor. The statistical analysis of the differential phosphorylation level can be done using multivariate and/or univariate statistical methods known in the art. The differential phosphorylation levels are obtained by (numerically) comparing the peptide phosphorylation levels or profiles in the presence and in the absence of the protein kinase inhibitor in the same sample, for instance, but not limited to, providing ratios or differences of the profiles obtained in the presence and the absence of the protein kinase inhibitor.

In addition, because the differential phosphorylation level is generated by comparing the phosphorylation levels or profiles of the same sample in the presence and the absence of the protein kinase inhibitor, preferably during a parallel series of measurements run in the same instrument, the differential phosphorylation level is surprisingly found to be less affected by variation, for example biological variation, experimental variation, compared to single phosphorylation levels or profiles. This provides a more robust, more sensitive, more reproducible and more reliable method for determining the survival prognosis of NSCLC. Moreover, the measurement of the kinase activity of said sample preferably occurs by contacting said sample with at least one protein kinase substrate in the presence and in the absence of a protein kinase inhibitor. Techniques from the prior art often require the incubation of the cells or tissues with said compounds preferably in vivo, during the culturing of the cells or tissues or during a large time period prior to the actual measurement of the kinase activity. The present invention provides that the protein kinase inhibitor is added directly to the sample and preferably directly to the lysate sample. The protein kinase inhibitors are added to the sample only just prior to contacting the sample with the protein kinase substrates and performing the kinase activity assay. Consequently, the protein kinase inhibitors are added in vitro at the time the incubation of the lysate sample with the protein kinase substrates is initiated. The present invention therefore provides an in vitro primary screening tool which allows the use of a single sample which is split into a first part that is used for the incubation of the sample in the absence of a protein kinase inhibitor while a second part of the sample is used for the incubation of the sample in the presence of a protein kinase inhibitor.

In another embodiment according to the present invention, the phosphorylation profiles comprise the phosphorylation levels of, preferably one or more, phosphorylation sites present in at least any of the peptide markers as listed in table 1. Preferably phosphorylation levels will be studied of phosphorylation sites present in at least 2, 3, 4, 5, 6, 7, 8, 9 10, 11, 12, 13, 14, 15, 16, 17, 18 or 19 of the peptide markers listed in Table 1.

The term "peptide markers" in the context of the present invention refers to the fact that the peptides as listed in Table 1 can be preferably used according to the methods of the present invention to measure the phosphorylation levels of phosphorylation sites of said markers in the presence of protein kinase present in samples. The phosphorylation levels of the individual phosphorylation sites present in said markers may be measured and compared in different ways. Therefore the present invention is not limited to the use of peptides identical to any of these peptide markers as listed in Table 1 as such. The skilled person may easily on the basis of the peptide markers listed in Table 1 design variant peptides compared to the specific peptides in said Table and use such variant peptides in a method for measuring phosphorylation levels of phosphorylation sites common to said peptide markers as listed in Table 1. These variant peptides may have one or more (2, 3, 4, 5, 6, 7, etc.) amino acids more or less than the given peptides and may also have amino acid substitutions (preferably conservative amino acid substitutions) as long as these variant peptides retain at least one or more of the phosphorylation sites of said original peptides as listed in said table. Further the skilled person may also easily carry out the methods according to the present invention by using proteins (full length or N- or C-terminally truncated) comprising the amino acid regions of the "peptide markers" listed in Table 1 as sources for studying the phosphorylation of sites present in the amino acid regions of the peptides listed in Table 1. Also the skilled person may use peptide mimetics.

The protein kinase substrates as used in the methods described herein, are meant to include peptides, proteins or peptide mimetics comprising, preferably one or more, of the phosphorylation sites of the peptide markers of Table 1. Said one or more phosphorylation sites are specifically phosphorylated by the protein kinases present in the sample thereby providing a phosphorylation profile. More preferably the protein kinase substrates (peptides, proteins or peptide mimetics) as used in the method of the present invention comprise, preferably one or more, of the phosphorylation sites present in at least two peptide markers as listed in Table 1. More particularly said protein kinase substrates represent the one or more phosphorylation sites present in at least 2, 3, 4, 5, 6, 7, 8, 9, 10, 11, 12, 13, 14, 15, 16, 17, 18 or 19 peptide markers as listed in Table 1. In a more preferred embodiment the protein kinase substrates comprise or consist of, preferably one or more, phosphorylation sites present in all of the peptide markers listed in Table 1.

A person skilled in the art will appreciate that the phosphorylation sites present in a single peptide marker as listed in Table 1 enable determining the survival prognosis of NSCLC patients. However, when the number of peptide markers as listed in Table 1 increases, so will increase the specificity and sensitivity of the method according to the present invention. When for example only one protein kinase substrate comprising the phosphorylation sites of a single peptide marker as listed in table 1 is used for the survival prognosis of a NSCLC patient the accuracy of the method will be lower, compared to a method where the survival prognosis of a NSCLC patient uses multiple protein kinase substrates comprising the phosphorylation sites of multiple peptide markers as listed in table 1. The highest method accuracy will be obtained when all protein kinase substrates comprising the phosphorylation sites of all peptide markers as listed in table 1 are used.

TABLE 1 list of 19 peptide markers comprising phosphorylation sites used for determining the kinase activity, their sequence and SEQ ID NO The name of the peptide markers refers to the associated proteins and also refers to the start and the end position of the amino acid sequence.

| Seq ID No | Name | Sequence |
|---|---|---|
| 1 | CBL_693_705 | EGEEDTEYMTPSS |
| 2 | LTK_669_681 | RDIYRASYYRRGD |
| 3 | CREB1_122_134 | QKRREILSRRPSY |
| 4 | TEC_512_524 | RYFLDDQYTSSSG |
| 5 | RAF1_331_343 | RPRGQRDSSYYWE |
| 6 | TYRO3_679_691 | KIYSGDYYRQGCA |
| 7 | NCF1_313_325 | QRSRKRLSQDAYR |
| 8 | MBP_259_271 | FGYGGRASDYKSA |
| 9 | ERBB2_1241_1253 | PTAENPEYLGLDV |
| 10 | ERBB2_870_882 | LDIDETEYHADGG |
| 11 | NPT2A_501_513 | AKALGKRTAKYRW |
| 12 | C1R_199_211 | TEASGYISSLEYP |
| 13 | NTRK1_489_501 | HIIENPQYFSDAC |
| 14 | NTRK2_699_711 | RDVYSTDYYRVGG |
| 15 | JAK1_1015_1027 | AIETDKEYYTVKD |
| 16 | VGFR2_944_956 | RFRQGKDYVGAIP |
| 17 | INSR_1348_1360 | SLGFKRSYEEHIP |
| 18 | PGFRB_771_783 | YMAPYDNYVPSAP |
| 19 | EGFR_1103_1115 | GSVQNPVYHNQPL |

It should further be noted that according to a preferred embodiment of the present invention the peptide markers as listed in Table 1 can be used as such for carrying out the methods according to the present invention. The present invention however also includes the use of analogs and combinations of these peptide markers for use in the method according to the present invention. The peptide marker analogs include peptide markers which show a sequence identity of more than 70%, preferably more than 80% and more preferably more than 90%.

In yet another embodiment, the present invention relates to a method according to the present invention wherein step (b) is replaced by steps (c) and (d) as provided below. The method according to the present invention may therefore comprise the steps of:

(a) measuring the kinase activity of a sample, obtained from the non-small cell lung tumor from said patient, in the presence and in the absence of a protein kinase inhibitor, thereby providing a phosphorylation profile of said sample in the presence of a protein kinase inhibitor and a phosphorylation profile of said sample in the absence of a protein kinase inhibitor;

(c) comparing said phosphorylation profile of said sample in the presence of a protein kinase inhibitor with said phosphorylation profile of said sample in the absence of a protein kinase inhibitor, thereby determining a classifier parameter; and, (d) determining the survival prognosis of said patient on the basis of said classifier parameter.

By establishing a classifier parameter for determining the survival prognosis of the NSCLC patient the method of the present invention provides a criterion for analysing the results obtained from the method of the present invention. This criterion enables a person to provide a diagnosis or prognosis on the basis of a single or limited number of data. The person providing the diagnosis or prognosis does not have to interpret an entire set of data, but rather bases his conclusion on the basis of a single or limited number of criteria.

The term "classifier parameter" as used herein represents a discriminating value which has been determined by establishing the phosphorylation profile in the presence and in the absence of a protein kinase inhibitor.

Said discriminating value identifies the survival prognosis of NSCLC patients. The classifier parameter includes information regarding the phosphorylation level of several protein kinase substrates. Classification is a procedure in which individual items are placed into groups based on quantitative information on one or more characteristics inherent in the items (e.g. phosphorylation levels or profiles of a sample) and based on a training set of previously labelled items (clinical response to a pharmacotherapy). The classifier parameter is calculated by applying a "classifier" to the measured phosphorylation levels of a sample. Based on the classifying parameter a sample is assigned to (or predicted to belong to) a class (determining the survival prognosis of NSCLC patients). The classifier has been previously determined by comparing samples which are known to belong to the respective relevant classes. For instance the classifier may be a mathematical function that uses information regarding the phosphorylation level of several protein kinase substrates which individual protein kinase substrates can be weighted based on the measured phosphorylation level of a number of protein kinase substrates (or values derived from that). Several methods are known in the art for developing a classifier including the neural network (Multi-layer Perceptron), support vector machines, k-nearest neighbours, Gaussian mixture model, naive bayes, decision tree, RBF classifiers, random forest, disciminant analysis, linear discriminant analysis, quadratic discriminant analysis, discriminant analysis—principal component analysis, partial least squares discriminant analysis, generalized distance regression and elastic net classification.

It is not relevant to give an exact threshold value for the classifier parameter. A relevant threshold value can be obtained by correlating the sensitivity and specificity and the sensitivity/specificity for any threshold value. A threshold value resulting in a high sensitivity results in a lower specificity and vice versa. If one wants to increase the positive predictive value of the test to predict short term NSCLC survivors, then threshold value can be changed which as a consequence will decrease the negative predictive value of the long term NSCLC survivors. If one wants to decrease the positive predictive value of the test to predict the short terms NSCLC survivors then the threshold value has to be changed in the opposite direction which as a consequence will increase the negative predictive value of the long term NSCLC survivors.

It is thus up to the diagnostic engineers to determine which level of positive predictive value/negative predictive value/sensitivity/specificity is desirable and how much loss in positive or negative predictive value is tolerable. The chosen threshold level could be dependent on other diagnostic parameters used in combination with the present method by the diagnostic engineers.

In yet another embodiment, the present invention relates to a method according to the present invention wherein said classifier parameter indicates a short term survival prognosis of said patient if said classifier parameter is above a first predetermined threshold level, and wherein said classifier parameter indicates a long term survival prognosis of said patient if said classifier parameter is below a second predetermined threshold level.

According to another embodiment, the present invention relates to the method of the present invention wherein said differential phosphorylation level or said classifier parameter indicates a short term, long term or undetermined or intermediate survival prognosis of said patient.

As used in the present application the survival prognosis of NSCLC patients is generally divided into two types of prognosis a short term or a long term survival prognosis and additionally some survival prognosis may be undetermined or intermediate. Whereas long term prognosis provides that the NSCLC patient will survive at least 5 years, the short term prognosis predicts that the NSCLC patient will not survive for more than 1 year unless further treatment is provided. The method of the present invention specifically enables the distinction between short term and long term survival. The survival prognosis however also provides information regarding the status and type of NSCLC and therefore also enables to provide the patient with an appropriate and best suited treatment.

In another embodiment, the present invention regards the method according to the present invention wherein said peptide markers are at least two of the peptide markers selected from the group consisting of the peptide markers with any of SEQ ID NO 1 to 19.

More preferably the present invention relates to a method according to the present invention wherein said protein kinase inhibitor is gefitinib.

As used herein, the term "protein kinase inhibitor" refers to a type of enzyme inhibitor which blocks the action of one or more protein kinases, hence they can be subdivided or characterised by peptides or proteins whose phosphorylation is inhibited. Examples of protein kinase inhibitors for use in the method of the present invention are Dasatinib (currently used for the treatment of leukaemia); erlotinib (currently used for the treatment of non-small cell lung cancer); gefitinib (currently used for the treatment of non-small cell lung cancer); imatinib (currently used for the treatment of gastrointestinal stromal tumors and leukaemia); lapatinib (currently used for the treatment of breast cancer); nilotinib (currently used for the treatment of leukaemia); sorafinib (currently used for the treatment of renal cell carcinoma and hepatocellular carcinoma; Sunitinib (currently used for the treatment of renal cell carcinoma); temsirolimus (currently used for the treatment of renal cell carcinoma); ABT-869; AEE788; Alvocidib; AP23464; AP23846; AP23848; ARRY-142886; ARRY-334543; AT-7519; Axitinib; AZD0530; AZD1152; BIBW-2992; BIRB-796; BMI-1026; BMS-599626; Bosutinib; Brivanib; Canertinib; CCT129202; Cediranib; CEP-7055; CP-547632; CP-724714; Dovitinib; E7080; Enzastaurin; everolimus; FI-700; Gossypol; HKI-272; HMN-176; HMN-214; INNO-406; JNJ-7706621; KRX-0601; LBW242; Lestaurtinib; Midostaurin; MK-0457; MLN8054; MP-470; Neratinib; ON0123380; ON01910; ON-01910; OSI-930; Pazopanib; PD166326; PD173955; PD180970; Pelitinib; PF-2341066; PHA665752; PHA-739358; PX-866; R-547; Seliciclib; Semapimod; Semaxanib; SNS-032; SU011248; SU014813; SU11248; SU11274; SU14813; Tandutinib; Telatinib; TSU-68; UCN-01; Vandetanib; Vatalanib; VE-465; ZM 447439 and protein kinase inhibitors used in research including Tyrphostin-1; Tyrphostin-23; Tyrphostin-51; Tyrphostin-63; AG-1007; AG-1112; AG-1433; RG-13022; SU-1498; I-OMe-Tyrphostin; AG-538; Protein Kinase G inhibitor peptide (Arg-Lys-Arg-Ala-Arg-Lys-Glu); Geldanamycin from *Streptomyces hygroscopicus;* Lavendustin A; and Genistein. More preferably a protein kinase inhibitor chosen from the group directed against the epidermal growth factor receptor including the protein kinase inhibitors gefitinib, erlotinib and/or lapatinib.

Additionally, the inventors have further found that by adding a second protein kinase inhibitor in step (a) of the method of the present invention allows further differentiation between the obtained phosphorylation profiles. When using both a first and a second protein kinase inhibitor while measuring the kinase activity, four different phosphorylation profiles can be obtained: a phosphorylation profile in the absence of any protein kinase inhibitors, a phosphorylation profile in the presence of the first protein kinase inhibitor, a phosphorylation profile in the presence of the second protein kinase inhibitor and a phosphorylation profile in the presence of the first and the second protein kinase inhibitor.

Another embodiment of the present invention relates to a method according to the present invention wherein said kinase substrates carrying phosphorylation sites are located or immobilized on a solid support, and preferably a porous solid support. Preferably said immobilized kinase substrates carrying phosphorylation sites will be immobilized proteins, peptides or peptide mimetics. In a preferred embodiment of the present invention peptides are immobilized on a solid support.

As used herein "peptide" refers to a short truncated protein generally consisting of 2 to 100, preferably 2 to 30, more preferably 5 to 30 and even more preferably 13 to 18 naturally occurring or synthetic amino acids which can also be further modified including covalently linking the peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds.

As used herein "protein" refers to a polypeptide made of amino acids arranged in a linear chain and joined together by peptide bonds between the carboxyl and amino groups of adjacent amino acid residues.

As used herein "peptide mimetics" refers to organic compounds which are structurally similar to peptides and similar to the peptide sequences list in Table 1. The peptide mimetics are typically designed from existing peptides to alter the molecules characteristics. Improved characteristics can involve, for example improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification.

For measuring the kinase activity of the sample a large variety of methods and formats are known in the art. The kinase activity can for example be measured using ELISA and multiplex ELISA techniques, blotting methods, mass spectrometry, capillary electrophoresis, bead arrays, macroarrays, microarrays or any other method known in the art. Depending on the type of kinase activity measurement method the solid support on which the proteins, peptides or peptide mimetics are fixed may vary. Whereas in ELISA the protein kinase substrates are attached to the surface of the microtiterplates, in microarrays the protein kinase substrates are immobilized on and/or in the microarray substrate.

In a preferred embodiment of the present invention the protein kinase substrates are immobilized on an array, and preferably a microarray of protein kinase substrates wherein the protein kinase substrates are immobilized onto a solid support or another carrier. The immobilization can be either the attachment or adherence of two or more protein kinase substrate molecules to the surface of the carrier including attachment or adherence to the inner surface of said carrier in the case of e.g. a porous or flow-through solid support.

In a preferred embodiment of the present invention, the array of protein kinase substrates is a flow-through array. The flow-through array as used herein could be made of any carrier material having oriented through-going channels as are generally known in the art, such as for example described in PCT patent publication WO 01/19517. Typically the carrier is made from a metal oxide, glass, silicon oxide or cellulose. In a particular embodiment the carrier material is made of a metal oxide selected from the group consisting of zinc oxide, zirconium oxide, tin oxide, aluminium oxide, titanium oxide and thallium; in a more particular embodiment the metal oxide consists of aluminium oxide.

Accordingly, in a further embodiment of the present invention said array is a Pamchip®.

In a further embodiment, the present invention relates to a method according to the present invention wherein said solid support (microarray) comprises any of the peptides as listed in Table 1 immobilized thereto.

In a further embodiment, the present invention relates to a method according to the present invention wherein said solid support (microarray) comprises each of the peptide as listed in Table 1 immobilized thereto.

Another embodiment of the present invention regards a method for predicting the response of a patient diagnosed with non-small cell lung cancer to a medicament, wherein the kinase activity of a sample, obtained from the non-small cell lung tumor from said patient, is measured in the presence and in the absence of said medicament and wherein said kinase activity in the presence said medicament is compared to the kinase activity in the absence of said medicament thereby determining the response of said patient to said medicament, wherein said kinase activity measurement provides phosphorylation profiles of said sample in the presence and in the absence of said medicament.

It should be noted that the observed response of the patient to said medicament can either be a positive response, wherein the medicament will improve the treatment of said patient, or a negative response, wherein the medicament has a negative or no influence on the treatment of said patient.

By measuring the kinase activity of a sample, obtained from the non-small cell lung tumor from said patient, in the presence and in the absence of a medicament, the effect of that medicament to the NSCLC can be assessed. This method was found particularly useful in the prediction of response to said medicament, and to enable the distinction between responders and non-responders in the treatment with said medicament. The measurement of the kinase activity of said sample preferably occurs by contacting said sample with at least one protein kinase substrate in the presence and in the absence of said medicament. Techniques from the prior art often require the incubation of the cells or tissues with said medicaments preferably in vivo, during the culturing of the cells or tissues or during a large time period prior to the actual measurement of the kinase activity. The present invention provides that the medicament is added directly to the sample and preferably directly to the lysate sample. The medicament is added to the sample only just prior to contacting the sample with the protein kinase substrates and performing the kinase activity assay. Consequently, the medicament is added in vitro at the time the incubation of the lysate sample with the protein kinase substrates is initiated. The present invention therefore provides an in vitro primary screening tool which allows the use of a single sample which is split into a first part that is used for the incubation of the sample in the absence of a medicament while a second part of the sample is used for the incubation of the sample in the presence of a medicament.

The medicament as used in the method of the present invention can be any kind of chemical substance for instance used in the treatment, cure, prevention, or diagnosis of disease or used to otherwise enhance physical or mental well-being. Specifically said medicament can be a kinase inhibitor, and more preferably a protein kinase inhibitor and most preferably a small molecule protein kinase inhibitor.

It is clear that effects of a medicament can be monitored using this method. The medicament affects the degree of inhibition, the potency and/or the selectivity of the kinases in the sample. More peptide inhibition is caused by the larger effect of the medicament on the kinases in the sample and therefore the drug is less selective. Also an increased peptide inhibition would lead to a larger amount of normal tissues being affected by the drug, making the drug less tumor tissue specific.

In another embodiment of the present invention the method for predicting the response of a patient diagnosed with non-small cell lung cancer to a medicament, uses phosphorylation profiles which comprise the phosphorylation levels of, preferably one or more, phosphorylation sites present in any of the peptide markers as listed in table 1. Preferably also this method will use two or more of said peptide markers as described above. More preferably this method will use at least 2, 3, 4, 5, 6, 7, 8, 9 10, 11, 12, 13, 14, 15, 16, 17, 18 or 19 of the peptide markers listed in Table 1.

Phosphorylation levels can also be measured according to the invention, without the necessity to generate phosphorylation profiles thereof. Also for this embodiment, the amount and the type of peptides, proteins or peptide mimetics to be used is as described above.

The present invention also relates according to another embodiment to an array for carrying out the method of the present invention, said array comprising immobilized proteins, peptides or peptide mimetics comprising, preferably one or more, phosphorylation sites present in any of the peptide markers as listed in table 1. More preferably said array comprises immobilized proteins, peptides or peptide mimetics comprising, preferably one or more, phosphorylation sites present in at least 2, 3, 4, 5, 6, 7, 8, 9 10, 11, 12, 13, 14, 15, 16, 17, 18 or 19 of the peptide markers listed in Table 1.

In a preferred embodiment said proteins, peptides or peptide mimetics are at least 25% of proteins, peptides or peptide mimetics on said array. Said arrays may further comprise one or more immobilized proteins, peptides or peptide mimetics which are used as calibration means for performing the methods according to the present invention.

More particularly said array comprises immobilized proteins, peptides or peptide mimetics comprising, preferably one or more, phosphorylation sites as described in detail above representing the peptide markers as listed in table 1. Additionally said proteins, peptides or peptide mimetics are preferably at least 25%, at least 50%, at least 70%, at least 80%, at least 90% or 100% of the proteins, peptides or peptide mimetics on said array.

The type of arrays to be used according to this embodiment are known in the art and are further detailed above.

The present invention also relates in another embodiment to a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method according to the present invention.

The present invention further relates to a computer system comprising a processor, and a memory coupled to said processor and encoding one or more programs, wherein said one or more programs instruct the processor to carry out the methods according to the present invention.

The present invention also relates in another embodiment to a kit for determining the survival prognosis of patients suffering from non-small cell lung cancer, comprising at least one array according to the present invention, and optionally a computer readable medium having recorded thereon one or more programs for carrying out the method according to the present invention.

The present invention further relates in yet another embodiment to a method for determining the survival prognosis of a patient suffering from non-small cell lung cancer, comprising the steps of:

(a) measuring the kinase activity of a sample, obtained from the non-small cell lung tumor from said patient, in the presence and in the absence of a protein kinase inhibitor, thereby providing the phosphorylation level of, preferably one or more, phosphorylation sites present in any of the peptide markers as listed in Table 1; and, (b) determining from said phosphorylation level in the presence and in the absence of a protein kinase inhibitor the survival prognosis of said patient.

Since the present inventors have identified a surprisingly useful set of peptide markers to be used in methods for determining the survival prognosis of a patient suffering from non-small cell lung cancer, the skilled man may carry out any method as defined above wherein he measures the kinase activity of any of the peptide markers of Table 1. Also this method may be carried out using the amount and type of peptides, proteins or protein mimetics as defined above. The formats for carrying out these methods are also as for the methods described above.

The present invention is hereafter exemplified by the illustration of particular, non-limiting examples.

EXAMPLES

Example 1

Example Showing Measurements of Kinase Activity of NSCLC Tumor Tissue in the Presence and in the Absence of the Protein Kinase Inhibitor Gefitinib The method of the present invention allows the measurement of the kinase activity in lysates prepared from fresh frozen NSCLC tumor tissue.

The inventors have surprisingly found that the survival prognosis can be classified by testing inhibition of kinase activity by studying kinase phosphorylation activity and inhibition levels in resection tissue from a tumor. The tumor content for each of the samples was higher than 70%, based on HE staining. 6 samples were taken from patients having a short survival (less than 9 months), 8 samples were taken from patients with a long survival period (over 95 months).

6 coupes of 10 μm thickness from tumor tissue were lysed in 100 microliter Mammalian Extraction Buffer (M-PER) containing phosphatase and protease inhibitors. After 30 minutes of lysis on ice, and centrifugation for 15 min at 4° C., the supernatants were aliquotted and frozen. For each sample 10 μg of protein diluted in the lysis solution, was pipetted into a reaction mixture composed of 1× ABL buffer (10× Abl buffer New England Biolabs, cat.nr B6050S −100 mM MgCl2, 10 mM EGTA, 20 mM DTT and 0.1% Brij 35 in 500 mM Tris/HCl, pH 7.5), 0.1% Bovine Serum Albumin, 100 μM ATP, 7.5 μg/ml anti-phosphotyrosine antibody to an end volume of 40 microliter. Before incubation of the lysate reaction mixtures on the PamChip substrate array a blocking step was carried out on the substrate arrays with 2% bovine serum albumin. After washing 3× with ABL buffer and loading of the lysate reaction mixtures into substrate arrays comprising 140 protein kinase substrates, including the 19 protein kinase peptide substrates as listed in Table 1, incubation was commenced thereby measuring the kinase activity of the sample. Each tumor tissue lysates was tested in three technical replicates on the substrate arrays without protein kinase inhibitor and in three technical replicates with 1 μM of protein kinase inhibitor gefitinib. During 60 cycles of pumping the lysate reaction mixture through the array, peptide phosphorylation was detected by an antibody present in the lysate reaction mixture. Real time data were obtained by measuring fluorescence of the bound anti-phosphotyrosine antibody after each 5 cycles. Images of the array were taken during the incubation of the array and after 60 cycles of incubation. After 60 cycles of incubation and imaging, the antibody mixture was removed and the array was washed. Images were collected at different exposure times. Signals for each spot on the image were quantified. Image quantification and data processing was conducted with dedicated PamGene software (Evolve and Bionavigator).

The results of the incubation of the NSCLC samples on a PamChip® with and without the protein kinase inhibitor gefitinib at a concentration of 1 μmol/L showed that the addition of gefitinib as protein kinase inhibitor provides a number of essential differences between the phosphorylation profiles with and without the protein kinase inhibitor, which enabled the differentiation between the different survival prognoses of NSCLC patients (data not shown).

The present example shows that the kinase activity profiles in combination with a kinase inhibitor clearly provide a differentiated phosphorylation profile.

Example 2

Example Showing the Survival Prognosis of NSCLC Patients

Tumor samples obtained from 2 classes of patients: short term survivors (6 samples) and long term survivors (8 samples) were incubated as described in example 1 on PamChip® arrays. The fluorescence from the spots in the images was quantified for quantitative purposes.

For each peptide the ratio of inhibited versus not inhibited signal was calculated and a one way ANOVA was performed to identify peptides with a significant difference between the long and short term survivors. Table 1 enlists 19 out of the 140 peptides that have a probability (p) for equal means over the 2 patient classes of $p < 0.01$. A heatmap showing the ratio of inhibited versus not inhibited phosphorylation signal in each of the peptide markers listed in Table 1, is provided in FIG. 1. Whereas the dotted squares indicate a positive ratio and the non-dotted squares a negative ratio, the grey intensity of the squares is proportional to the ratio level.

The present example shows that the kinase activity profiles in combination with a kinase inhibitor can be used to identify early stage NSCLC patients with poor prognosis. The fact that a distinction can be made between long and short term survivors, based on effect of inhibitor gefitinib in the patients proves that the use of the peptide set as listed in Table 1 enables to determine the survival prognosis in NSCLC and according to the prognosis select patients that might benefit from specific adjuvant therapy.

---

The invention claimed is:

1. A method for determining the survival prognosis of a patient suffering from non-small cell lung cancer, comprising the steps of:
(a) measuring kinase activity of a sample, obtained from the non-small cell lung tumor from said patient, by contacting said sample in the presence and in the absence of a protein kinase inhibitor with at least the peptide markers consisting of SEQ ID NO: 1 to 19, and obtaining phosphorylation of phosphorylation sites present in said sequences, thereby providing a phosphorylation profile of said sample in the presence of a protein kinase inhibitor and a phosphorylation profile of said sample in the absence of a protein kinase inhibitor,
wherein said peptide markers are immobilized on an array; and
(b) determining from said phosphorylation profiles in the presence and in the absence of a protein kinase inhibitor the differential phosphorylation level, said differential phosphorylation level indicating the survival prognosis of said patient.

2. The method according to claim 1, wherein step (b) comprises comparing said phosphorylation profile of said sample in the presence of a protein kinase inhibitor with said phosphorylation profile of said sample in the absence of a protein kinase inhibitor, thereby determining a classifier parameter, said classifier parameter indicating a survival prognosis of less than 1 year for said patient if said classifier parameter is above a first predetermined threshold level, and said classifier parameter indicating a survival prognosis of at least 5 years for said patient if said classifier parameter is below a second predetermined threshold level; and a step of determining the survival prognosis of said patient on the basis of said classifier parameter.

3. The method according to claim 2, wherein said classifier parameter indicates a survival prognosis of less than 1 year, a survival prognosis of at least 5 years or a survival prognosis between 1 year and 5 years for said patient.

4. The method according claim 1, wherein said differential phosphorylation level indicates a survival prognosis of less than 1 year, a survival prognosis of at least 5 years or a survival prognosis between 1 year and 5 years for said patient.

5. The method according claim 1, wherein said protein kinase inhibitor is gefitinib.

6. The method according to claim 1, wherein the array is a porous array.

7. A method for determining the survival prognosis of a patient suffering from non-small cell lung cancer, comprising the steps of:
(a) measuring the kinase activity of a sample, obtained from the non-small cell lung tumor from said patient, by contacting said sample in the presence and in the absence of a protein kinase inhibitor with at least the peptide markers consisting of SEQ ID NO: 1 to 19, and obtaining phosphorylation of phosphorylation sites present in said sequences, thereby providing the phosphorylation level of said sample in the presence of a protein kinase inhibitor and a phosphorylation level of said sample in the absence of a protein kinase inhibitor, wherein said peptide markers are immobilized on an array; and,
(b) determining from said phosphorylation level in the presence and in the absence of a protein kinase inhibitor the survival prognosis of said patient.

8. The method according to claim 7, wherein the array is a porous array.

* * * * *

SEQUENCE LISTING

<160> NUMBER OF SEQ ID NOS: 19

<210> SEQ ID NO 1
<211> LENGTH: 13
<212> TYPE: PRT
<213> ORGANISM: Artificial Sequence
<220> FEATURE:
<223> OTHER INFORMATION: Peptide CBL_693_705

<400> SEQUENCE: 1

Glu Gly Glu Glu Asp Thr Glu Tyr Met Thr Pro Ser Ser
1               5                   10

<210> SEQ ID NO 2
<211> LENGTH: 13
<212> TYPE: PRT

```
<213> ORGANISM: Artificial Sequence
<220> FEATURE:
<223> OTHER INFORMATION: Peptide LTK_669_681

<400> SEQUENCE: 2

Arg Asp Ile Tyr Arg Ala Ser Tyr Tyr Arg Arg Gly Asp
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide CREB1_122_134

<400> SEQUENCE: 3

Gln Lys Arg Arg Glu Ile Leu Ser Arg Arg Pro Ser Tyr
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Peptide TEC_512_524

<400> SEQUENCE: 4

Arg Tyr Phe Leu Asp Asp Gln Tyr Thr Ser Ser Ser Gly
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Peptide RAF1_331_343

<400> SEQUENCE: 5

Arg Pro Arg Gly Gln Arg Asp Ser Ser Tyr Tyr Trp Glu
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Peptide TYRO3_679_691

<400> SEQUENCE: 6

Lys Ile Tyr Ser Gly Asp Tyr Tyr Arg Gln Gly Cys Ala
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Peptide NCF1_313_325

<400> SEQUENCE: 7

Gln Arg Ser Arg Lys Arg Leu Ser Gln Asp Ala Tyr Arg
1               5                   10

<210> SEQ ID NO 8
<211> LENGTH: 13
<212> TYPE: PRT
<213> ORGANISM: Artificial Sequence
```

```
<220> FEATURE:
<223> OTHER INFORMATION: Peptide MBP_259_271

<400> SEQUENCE: 8

Phe Gly Tyr Gly Gly Arg Ala Ser Asp Tyr Lys Ser Ala
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Peptide ERBB2_1241_1253

<400> SEQUENCE: 9

Pro Thr Ala Glu Asn Pro Glu Tyr Leu Gly Leu Asp Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Peptide ERBB2_870_882

<400> SEQUENCE: 10

Leu Asp Ile Asp Glu Thr Glu Tyr His Ala Asp Gly Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Peptide NPT2A_501_513

<400> SEQUENCE: 11

Ala Lys Ala Leu Gly Lys Arg Thr Ala Lys Tyr Arg Trp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Peptide C1R_199_211

<400> SEQUENCE: 12

Thr Glu Ala Ser Gly Tyr Ile Ser Ser Leu Glu Tyr Pro
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Peptide NTRK1_489_501

<400> SEQUENCE: 13

His Ile Ile Glu Asn Pro Gln Tyr Phe Ser Asp Ala Cys
1               5                   10

<210> SEQ ID NO 14
<211> LENGTH: 13
<212> TYPE: PRT
<213> ORGANISM: Artificial Sequence
<220> FEATURE:
```

```
<223> OTHER INFORMATION: Peptide NTRK2_699_711

<400> SEQUENCE: 14

Arg Asp Val Tyr Ser Thr Asp Tyr Tyr Arg Val Gly Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Peptide JAK1_1015_1027

<400> SEQUENCE: 15

Ala Ile Glu Thr Asp Lys Glu Tyr Tyr Thr Val Lys Asp
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Peptide VGFR2_944_956

<400> SEQUENCE: 16

Arg Phe Arg Gln Gly Lys Asp Tyr Val Gly Ala Ile Pro
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Peptide INSR_1348_1360

<400> SEQUENCE: 17

Ser Leu Gly Phe Lys Arg Ser Tyr Glu Glu His Ile Pro
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Peptide PGFRB_771_783

<400> SEQUENCE: 18

Tyr Met Ala Pro Tyr Asp Asn Tyr Val Pro Ser Ala Pro
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Peptide EGFR_1103_1115

<400> SEQUENCE: 19

Gly Ser Val Gln Asn Pro Val Tyr His Asn Gln Pro Leu
1               5                   10
```